United States Patent [19]
Katsumata et al.

[11] Patent Number: 5,643,769
[45] Date of Patent: Jul. 1, 1997

[54] PROCESS FOR PRODUCING AN OPTICALLY ACTIVE γ-HYDROXY-L-GLUTAMIC ACID

[75] Inventors: Ryoichi Katsumata; Shinichi Hashimoto, both of Machida, Japan

[73] Assignee: Kyowa Hakko Kogyo Co., Ltd., Tokyo, Japan

[21] Appl. No.: 501,177

[22] Filed: Jul. 11, 1995

[30] Foreign Application Priority Data

Jul. 11, 1994 [JP] Japan ................................ 6-158656

[51] Int. Cl.$^6$ ...................... C12P 13/04; C12P 13/14; C12P 41/00
[52] U.S. Cl. .................. 435/106; 435/110; 435/252.3; 435/252.31; 435/252.33; 435/280
[58] Field of Search ..................... 435/110, 280, 435/106, 252.3, 252.33, 252.31

[56] References Cited

FOREIGN PATENT DOCUMENTS 0206904  12/1986  European Pat. Off. .

OTHER PUBLICATIONS

J. Am. Chem. Soc. vol. 79 pp. 6192–6198 Benoiton et al Published Dec. 5, 1957.

Adams et al "Biochim. & Biophys. Acta" 77 (1963) 133–135.

Adams et al "Jour. Biol. Chem" vol. 235 No. 12 Dec. 1960 pp. 3504–3512.

Passerat et al "Tetrahed. Letters" vol. 28 #12 pp. 1277–1280 (1980).

"Methods in Enzymology" Metabolism of Amino Acids & Amines vol. XVIIB pp. 274–281 Academic Press ed. Tabor et al 1971.

Methods in Enzymology, vol. 17, No. B, 1970, pp. 266–306, E. Adams, "Enzymes and Intermediates of Hydroxyproline Degradation", pp. 266–268.

*Primary Examiner*—Herbert J. Lilling
*Attorney, Agent, or Firm*—Antonelli, Terry, Stout & Kraus, LLP

[57] ABSTRACT

An object of the present invention is to provide a process for producing an optically active γ-hydroxy-L-glutamic acid advantageously on an industrial scale. The present invention provides a process for producing an optically active γ-hydroxy-L-glutamic acid, which comprises allowing biocatalyst I, an amino group donor, pyruvic acid and glyoxylic acid to coexist in an aqueous medium to form the optically active γ-hydroxy-L-glutamic acid in the aqueous medium, and collecting the formed optically active γ-hydroxy-L-glutamic acid therefrom, said biocatalyst I having activity of forming the optically active γ-hydroxy-L-glutamic acid from pyruvic acid and glyoxylic acid in the presence of an amino group donor. The present invention also provides a process for producing an optically active γ-hydroxy-L-glutamic acid, which comprises allowing biocatalyst II, an amino group donor and optically active 4-hydroxy-2-ketoglutaric acid to coexist in an aqueous medium to form the optically active γ-hydroxy-L-glutamic acid in the aqueous medium, and collecting the formed optically active 4-hydroxy-2-ketoglutaric acid therefrom, said biocatalyst II having activity of converting an optically active 4-hydroxy-2-ketoglutaric acid into the optically active γ-hydroxy-L-glutamic acid in the presence of an amino group donor.

16 Claims, No Drawings

PROCESS FOR PRODUCING AN OPTICALLY ACTIVE γ-HYDROXY-L-GLUTAMIC ACID

BACKGROUND OF THE INVENTION

1. Field of the Invention

The present invention relates to a process for producing an optically active γ-hydroxy-L-glutamic acid, that is, threo-γ-hydroxy-L-glutamic acid [(2S,4S)-4-hydroxyglutamic acid] or erythro-γ-hydroxy-L-glutamic acid [(2S,4R)-4-hydroxyglutamic acid].

An optically active γ-hydroxy-L-glutamic acid is known to have activity of inhibiting glutamine synthetase [Khim-Farm. Zh., 18, 655 (1984)] or incorporation of glutamic acid by presynaptic vesicle [Neurochem. Res., 18, 79 (1993)], and it is useful as a reagent for investigation of the above-mentioned enzyme or organ. Further, this acid is useful as a medicament based on the above-mentioned activity.

2. Prior Art

As a conventional method for producing an optically active γ-hydroxy-L-glutamic acid, known are a method in which the optically active γ-glutamic acid is separated from a mixture of four kinds of isomers of γ-hydroxyglutamic acid which is chemically synthesized from ethyl-α-acetoxy-β-chloropropionic acid and ethylacetamidocyanic acid, a method in which the optically active γ-glutamic acid is separated from a mixture of threo- and erythro-γ-hydroxy-L-glutamic acids formed by reacting DL-4-hydroxy-2-ketoglutaric acid and ammonia with glutamic acid dehydrogenase derived from mammal liver in the presence of NADPH [Biochem. Biophis. Acta., 77, 133 (1963)], a method in which threo-γ-hydroxy-L-glutamic acid [(2S,4S)-4-hydroxyglutamic acid] is extracted from Phlox decussata (Methods in Enzymology, 17, part B, 277), a method in which L-4-hydroxy-2-ketoglutaric acid reacts with cisteine-sulfinic acid in the presence of transaminase to form threo-γ-hydroxy-L-glutamic acid [Tetrahedron Lett., 28, 1277 (1987)], and a method in which the optically active γ-glutamic acid is formed by reacting $\Delta^1$-pyrroline-3-hydroxy-5-carboxylate with $\Delta^1$-pyrroline dehydrogenase derived from bovine liver [J. Biochem., 235, 3504 (1960)].

The conventional methods for producing an optically active γ-hydroxy-L-glutamic acid involve the following defects.

(1) The starting materials are expensive.

(2) A step of separating isomers is required and the cost is high.

(3) A yield is low.

Accordingly, the development of a method for producing the optically active γ-hydroxy-L-glutamic acid advantageously on an industrial scale has been in demand.

SUMMARY OF THE INVENTION

It is an object of the present invention to provide a process for producing an optically active γ-hydroxy-L-glutamic acid advantageously on an industrial scale.

The present invention provides a process for producing an optically active γ-hydroxy-L-glutamic acid, which comprises allowing a biocatalyst (hereinafter referred to as "biocatalyst I"), an amino group donor, pyruvic acid and glyoxylic acid to coexist in an aqueous medium to form the optically active γ-hydroxy-L-glutamic acid in the aqueous medium, and collecting the formed optically active γ-hydroxy-L-glutamic acid therefrom (hereinafter referred to as "process I"), said biocatalyst I having activity of forming the optically active γ-hydroxy-L-glutamic acid from pyruvic acid and glyoxylic acid in the presence of an amino group donor.

The present invention also provides a process for producing an optically active γ-hydroxy-L-glutamic acid, which comprises allowing a biocatalyst (hereinafter referred to as "biocatalyst II"), an amino group donor and optically active 4-hydroxy-2-ketoglutaric acid to coexist in an aqueous medium to form the optically active γ-hydroxy-L-glutamic acid in the aqueous medium, and collecting the formed optically active γ-hydroxy-L-glutamic acid therefrom (hereinafter referred to as "process II"), said biocatalyst II having activity of converting an optically active 4-hydroxy-2-ketoglutaric acid into the optically active γ-hydroxy-L-glutamic acid in the presence of an amino acid donor.

The optically active γ-hydroxy-L-glutamic acid is threo-γ-hydroxy-L-glutamic acid [(2S,4S)-4-hydroxyglutamic acid] or erythro-γ-hydroxy-L-glutamic acid [(2S,4R)-4-hydroxyglutamic acid], and the optically active 4-hydroxy-2-ketoglutaric acid is L-4-hydroxy-2-ketoglutaric acid [(S)-hydroxy-2-ketoglutaric acid] or D-4-hydroxy-2-ketoglutaric acid [(R)-hydroxy-2-ketoglutaric acid].

More specifically, the present invention provides a process for producing threo- or erythro-γ-hydroxy-L-glutamic acid, which comprises allowing biocatalyst I, amino group donor, pyruvic acid and glyoxylic acid to coexist in an aqueous medium to form threo- or erythro-γ-hydroxy-L-glutamic acid in the aqueous medium, and collecting the formed threo- or erythro-γ-hydroxy-L-glutamic acid from the aqueous medium, and a process for producing threo- or erythro-γ-hydroxy-L-glutamic acid, which comprises allowing biocatalyst II, amino group donor and L- or D-4-hydroxy-2-ketoglutaric acid to coexist in an aqueous medium to form threo- or erythro-γ-hydroxy-L-glutamic acid in the aqueous medium, and collecting the formed threo- or erythro-γ-hydroxy-L-glutamic acid from the aqueous medium.

DETAILED DESCRIPTION OF THE INVENTION

The present invention will be described in detail below.

In process I, "process I-(1)" means a process for producing threo-γ-hydroxy-L-glutamic acid, which comprises allowing biocatalyst I, an amino group donor, pyruvic acid and glyoxylic acid to coexist in an aqueous medium to form threo-γ-hydroxy-L-glutamic acid in the aqueous medium, and collecting the formed threo-γ-hydroxy-L-glutamic acid from the aqueous medium, and "process I-(2)" means a process for producing erythro-γ-hydroxy-L-glutamic acid, which comprises allowing biocatalyst I, an amino group donor, pyruvic acid and glyoxylic acid to coexist in an aqueous medium to form erythro-γ-hydroxy-L-glutamic acid in the aqueous medium, and collecting the formed erythro-γ-hydroxy-L-glutamic acid from the aqueous medium.

Biocatalyst I used in process I includes a culture, cells, processed cells, purified enzyme and crude enzyme of a microorganism. Any microorganism can be used so long as it has activity of forming the optically active γ-hydroxy-L-glutamic acid from pyruvic acid and glyoxylic acid in the presence of the amino group donor.

Examples of the microorganism include microorganisms which belong to the genus Pseudomonas, Paracoccus, Providencia, Rhizobium, Morganella, Enterobacter, Arthrobacter, Caulobacter, Microbacterium,

*Curtobacterium, Brevibacterium, Corynebacterium, Clavibacter* or *Bacillus*, and mutants and derivatives of these microorganisms.

As biocatalyst I used in process I-(1), any microorganism can be used so long as it has activity of forming the optically active γ-hydroxy-L-glutamic acid from pyruvic acid and glyoxylic acid in the presence of the amino group donor. Preferable examples of the microorganism include microorganisms which belong to the genus *Pseudomonas, Paracoccus, Providencia, Rhizobium, Morganella, Enterobacter, Arthrobacter, Caulobacter, Microbacterium, Curtobacterium, Brevibacterium, Corynebacterium* or *Clavibacter*.

Specific examples of the microorganism include *Pseudomonas putida* ATCC 795, *Pseudomonas putida* ATCC 4359, *Pseudomonas oleovorans* ATCC 8062, *Pseudomonas saccharophila* ATCC 15946, *Pseudomonas boreopolis* ATCC 15452, *Pseudomonas taetorolens* ATCC 17466, *Paracoccus denitrificans* ATCC 19367, *Providencia rustigianii* ATCC 13159, *Rhizobium meliloti* FERM BP-4582, *Morganella morganii* ATCC 25830, *Enterobacter aerogenes* ATCC 13048, *Arthrobacter crystallopoietes* ATCC 154821, *Caulobacter crescentus* ATCC 19089, *Microbacterium imperiale* ATCC 8365, *Curtobacterium citreum* ATCC 15828, *Brevibacterium ammoniagenes* ATCC 6871, *Clavibacter michiganense* ATCC 10202, *Clavibacter rathayi* ATCC 13659, and *Clavibacter tritici* ATCC 11402.

As biocatalyst I used in process I-(2), a microorganism which belongs to the genus *Bacillus* and has activity of forming erythro-γ-hydroxy-L-glutamic acid from pyruvic acid and glyoxylic acid in the presence of the amino group donor is preferably employed.

For example, *Bacillus* sp. S16 (FERM BP-4647) can be employed.

Biocatalyst II used in process II includes a culture, cells, processed cells, purified enzyme and crude enzyme of a microorganism. Any microorganism can be used so long as it has activity of converting the optically active 4-hydroxy-2-ketoglutaric acid into the optically active γ-hydroxy-L-glutamic acid in the presence of the amino group donor.

Examples of a microorganism include microorganisms which belong to the genus *Escherichia, Serratia, Pseudomonas, Arthrobacter* or *Corynebacterium*, and mutants and derivatives of these microorganisms.

Specific examples of a microorganism include *Escherichia coli* ATCC 33625, *Serratia marcesens* ATCC 13880, *Pseudomonas chlororaphis* ATCC 9446, *Arthrobacter protophormlae* ATCC 19271, and *Corynebacterium glutamicum* ATCC 13032.

Particularly, a mutant in which at least one of α-ketoglutaric acid dehydrogenase activity and optically active 4-hydroxy-2-ketoglutaric acid degrading activity is deleted or decreased compared to its parent strain can be preferably employed.

Such a mutant can be obtained by mutagenizing a parent strain with a usual mutagenizing agent such as N-methyl-N'-nitro-N-nitrosoguanidine (NTG) or by irradiation with UV light or γ-rays, spreading the mutagenized cells onto a suitable agar plate medium, obtaining the grown mutant, and selecting a strain in which at least one of α-ketoglutaric acid dehydrogenase activity and optically active 4-hydroxy-2-ketoglutaric acid degrading activity is deleted or decreased compared to its parent strain.

As a parent strain for obtaining such a mutant, any microorganism can be used so long as it has activity of converting the optically active 4-hydroxy-2-ketoglutaric acid into the optically active γ-hydroxy-L-glutamic acid. Especially, preferable one is *Escherichia coli* ATCC 33625 which is a sub-strain of *Escvherichia coli* K-12.

Specific examples of the mutant include *Escherichia coli* HKK2 (sucA, iclR, trp) which lacks α-ketoglutaric acid dehydrogenase activity and *Escherichia coli* HKK27 which lacks α-ketoglutaric acid dehydrogenase activity and decreases L-4-hydroxy-2-ketoglutaric acid degrading activity. *Escherichia coli* HKK27 strain was deposited with the National Institute of Bioscience and Human Technology, Agency of Industrial Science and Technology, Japan, on May 31, 1994 as FERM BP-4681, under the Budapest Treaty.

Using the microorganism used for biocatalyst I or II as the parent strain, a mutant having stronger glutamic acid dehydrogenase activity than the parent strain is obtained. Using this mutant, the optically active γ-hydroxy-L-glutamic acid can be produced more efficiently than using the parent strain.

Such a mutant can be obtained by mutagenizing the parent strain with a usual mutagenizing agent such as NTG or by irradiation with UV light or γ-rays, spreading the mutagenized cells onto a suitable agar plate medium, obtaining the grown mutant, and selecting the strain having stronger glutamic acid dehydrogenase activity than the parent strain. Further, the mutant can be also obtained by transforming the parent strain with a recombinant DNA of a DNA fragment containing a glutamic acid dehydrogenase gene derived from a strain having glutamic acid dehydrogenase activity and a vector DNA.

For example, this recombinant strain can be obtained by transforming *Escherichia coli* with a recombinant DNA of a DNA fragment containing a glutamic acid dehydrogenase gene derived from the microorganism of the genus *Escherichia*, especially *Escherichia coli* and a vector DNA.

As a microorganism which is a supply source of the glutamic acid dehydrogenase gene, any microorganism can be employed so long as it has glutamic acid dehydrogenase activity. *Escherichia coli* is especially preferable. For example, *Escherichia coli* ATCC 33625, which is a sub-strain of *Escherichia coli* K-12, is preferable.

The glutamic acid dehydrogenase gene can be isolated from the microorganism by the conventional method [Biochem. Biophys. Acta, 72, 619 (1963), Molecular Cloning, A Laboratory Manual, 2nd edition, Cold Spring Harbor Laboratory Press, (1989)].

As a vector, any phage vector or plasmid vector can be employed so long as it can be replicated autonomously in a host microorganism. For example, pBR322 can be employed.

The recombinant DNA of the DNA fragment containing glutamic acid dehydrogenase gene and the vector DNA can be obtained by cleaving both of the DNAs in a test tube with a restriction endonuclease that gives the same cleavage terminals, and ligating the cleaved DNAs with a DNA ligase.

As a host microorganism, any microorganism can be employed so long as it has ability of incorporating a DNA. Examples of the microorganism include wild strains and mutants having a chemical resistance and nutritional requirement.

The recombinant plasmid containing the glutamic acid dehydrogenase gene can be obtained by transforming the host microorganism with the recombinant DNA of the DNA fragment containing the glutamic acid dehydrogenase gene and of the vector DNA, selecting the transformant containing the recombinant DNA, and isolating the plasmid from the transformant. The transformation can be carried out by Maniatis et al. method [Molecular Cloning, A Laboratory Manual, 250 (1982)]. The recombinant plasmid can be isolated from the cultured cells of the transformant by Maniatis et al. method [Molecular Cloning, A Laboratory Manual), 86 (1982)].

Using the obtained recombinant plasmid, the microorganism which can be used as biocatalyst I or II is transformed by Maniatis et al. method to obtain the intended transformant having increased glutamic acid dehydrogenase activity.

Specifically, *Escherichia Coli* HKK27/pHK10 is an example of a strain which has both of the mutations, that is, the lack of α-ketoglutaric acid dehydrogenase and the decrease in L-4-hydroxy-2-ketoglutaric acid degrading activity and which has increased glutamic acid dehydrogenase activity. *Escherichia Coli* HKK27/pHK10 was deposited with the National Institute of Bioscience and Human Technology, Japan, Agency of Industrial Science and Technology on May 31, 1994 as FERM BP-4682, under the Budapest Treaty.

The microorganism used as biocatalyst I or II can be cultured by the usual method.

The medium for cultivating these microorganism may be any of a natural medium and a synthetic medium so long as it contains a carbon source, a nitrogen source, an inorganic salt, and the like that can be assimilated by the microorganism used and the microorganism can be thereby cultured efficiently.

Any carbon source can be employed so long as it can be assimilated by the microorganism used. Examples of the carbon source include sugar such as glucose, fructose, sucrose, maltose, starch, starch hydrolysates and molasses; organic acids such as acetic acid, lactic acid and gluconic acid; and alcohols such as ethanol and propanol.

Any nitrogen source can be employed so long as it can be assimilated by the microorganism used. Examples of the nitrogen source include ammonia, ammonium salts of inorganic and organic acids such as ammonium sulfate, ammonium chloride, ammonium acetate and ammonium phosphate, other nitrogen-containing compounds, peptone, meat extract, yeast extract, corn steep liquor, casein hydrolysates, soybean cakes, soybean cake hydrolysates, fermented cells, and digested products thereof.

Any inorganic salt can be employed so long as it can be assimilated by the microorganism used. Examples of the inorganic salts include potassium dihydrogen phosphate, dipotassium hydrogen phosphate, ammonium sulfate, ammonium chloride, sodium chloride, magnesium sulfate, ferrous sulfate and manganese sulfate. Trace elements such as calcium, zinc, boron, copper, cobalt and molybdenum may be added to the culture medium. Further, vitamins such as thiamine and biotin, amino acids such as glutamic acid and aspartic acid, and nucleic acid-related compounds such as adenine and guanine may be added to the culture medium, if necessary.

The cultivation of the microorganism is carried out under aerobic conditions such as shaking culture and submerged-aerial stirring culture. It is advisable that the culturing be carried out at a temperature of 15° to 37° C. for 10 to 96 hours.

A pH is maintained at 5.0 to 9.0 during the cultivation. The pH is adjusted with an inorganic or organic acid, alkaline solution, urea, calcium carbonate or ammonia.

The processed cells of the microorganism used as biocatalyst I or II include a dried cells, lyophilized cells, surfactant- or organic solvent-treated cells, enzymatically-treated cells, ultrasonically-treated cells, mechanically compressed cells, cellular protein fractions, and immobilized product of unprocessed cells or processed cells.

In processes I and II of the present invention, the amino group donor used includes ammonia, inorganic ammonium salts such as ammonium sulfate, ammonium chloride and urea, and amino acids such as aspartic acid. The concentration of the amino group donor is 0.1 to 100 g/liter, preferably 1 to 10 g/liter.

Examples of the aqueous medium used in process I and II of the present invention include water; buffers such as a phosphate buffer, carbonate buffer, acetate buffer, borate buffer, citrate buffer and tris buffer; and aqueous solutions containing organic solvents, for example, alcohols such as methanol and ethanol, esters such as ethyl acetate, ketones such as acetone, amides such as acetamide. If necessary, a surfactant such as Triton X-100 (made by Nacalai Tesque, Inc.) or Nonion HS204 (made by Nippon Oils & Fats Co., Ltd.), or an organic solvent such as toluene and xylene may be added to the aqueous medium in an amount of approximately 0.1 to 20 g/liter.

The concentration of pyruvic acid or glyoxylic acid used in process I of the present invention is 1 to 200 g/liter, preferably 20 to 200 g/liter. The compound capable of being converted into pyruvic acid by biocatalyst I can replace pyruvic acid. Examples of such a compound include sugars such as glucose, fructose, sucrose, maltose, starch, starch hydrolysates and molasses; and organic acids such as acetic acid, lactic acid and gluconic acid.

The concentration of biocatalyst I is 0.1 to 200 g/liter, preferably 5 to 100 g/liter (calculated in terms of the cells of the microorganism).

The optically active γ-hydroxy-L-glutamic acid can be produced by adding biocatalyst I, amino group donor, pyruvic acid and glyoxylic acid at the above concentrations to the aqueous medium, and reacting the mixture at a temperature of 15° to 80° C., preferably 25° to 60° C. for 30 minutes to 80 hours at a pH of 3 to 11, preferably 5 to 9.

In process I, the optically active γ-hydroxy-L-glutamic acid can be also produced by adding the amino group donor, pyruvic acid and glyoxylic acid at the above-mentioned concentrations to the aqueous medium at the starting point of, or during, the culturing of the microorganism used as biocatalyst I.

In process II of the present invention, any of a purified product or a crude product of the optically active 4-hydroxy-2-ketoglutaric acid can be used. The optically active 4-hydroxy-2-ketoglutaric acid formed by the reaction in the presence of the biocatalyst derived from the microorganism or the reaction solution containing the optically active 4-hydroxy-2-ketoglutaric acid can be employed. A process of producing the optically active 4-hydroxy-2-ketoglutaric acid by the reaction in the presence of the biocatalyst derived from the microorganism will be described later. The concentration of the optically active 4-hydroxy-2-ketoglutaric acid used is 1 to 200 g/liter, preferably 20 to 200 g/liter.

The concentration of biocatalyst II is 0.1 to 200 g/liter, preferably 5 to 100 g/liter (calculated in terms of microorganism cells).

The optically active γ-hydroxy-L-glutamic acid can be produced by adding biocatalyst II, amino group donor and optically active 4-hydroxy-2-ketoglutaric acid at the above-mentioned concentrations to the aqueous medium, and reacting the mixture at a temperature of 15° to 80° C., preferably 25° to 60° C. for 30 minutes to 80 hours at a pH of 3 to 11, preferably 5 to 9.

In process II, the optically active γ-hydroxy-L-glutamic acid can be also produced by adding the amino group donor and optically active 4-hydroxy-2-ketoglutaric acid at the above-mentioned concentrations to the aqueous medium at the starting point of, or during, the culturing of the microorganism used as biocatalyst II.

The optically active γ-hydroxy-L-glutamic acid produced by process I or II can be isolated by a conventional method of purifying amino acids. For instance, the optically active γ-hydroxy-L-glutamic acid can be isolated from the supernatant of the reaction solution from which the solids are removed by centrifugation through a combination of treatments with an ion exchange resin, membrane, and the like.

[Production of the optically active 4-hydroxy-2-ketoglutaric acid by the reaction in the presence of the biocatalyst derived from the microorganism]

The optically active 4-hydroxy-2-ketoglutaric acid can be produced by allowing a biocatalyst (hereinafter referred to as "biocatalyst III") that has an activity of forming the optically active 4-hydroxy-2-ketoglutaric acid from pyruvic acid and glyoxylic acid, pyruvic acid and glyoxylic acid to coexist in an aqueous medium to convert glyoxylic acid into the optically active 4-hydroxy-2-ketoglutaric acid.

Biocatalyst III used in the above-mentioned production includes a culture, cells, processed cells, purified enzyme and crude enzyme of a microorganism. Any microorganism can be employed so long as it has activity of forming the optically active 4-hydroxy-2-ketoglutaric acid from pyruvic acid and glyoxylic acid.

Specific examples of such microorganism include microorganisms that belong to the genus *Cellvibrio, Bacillus, Pseudomonas, Paracoccus, Providencia, Rhizobium* or *Morganella*.

When producing D-4-hydroxy-2-ketoglutaric acid, the microorganisms that belong to the genus *Cellvibrio* or *Bacillus* are especially preferable.

Specific examples thereof include *Cellvibrio gilvus* ATCC 13127, *Bacillus* sp. OC187, and *Bacillus* sp. S16. The ATCC 13127 and *Bacillus* sp. OC187 can be deprived of activity of forming L-4-hydroxy-2-ketoglutaric acid by heat-treating these strains at 60° to 90° C. for 15 minutes to 2 hours. The strains deprived of activity of forming the L-4-hydroxy-2-ketoglutaric acid can be obtained by mutagenizing microorganisms belonging to the genus *Cellvibrio* or *Bacillus* and having activity of forming D-4-hydroxy-2-ketoglutaric acid from pyruvic acid or a compound capable of being converted into pyruvic acid by the microorganism and glyoxylic acid, by a conventional mutation treatment such as NTG, and screening the mutants deprived of the activity of forming L-4-hydroxy-2-ketoglutaric acid. *Bacillus* sp. S16 is a mutant which is derived from *Bacillus* sp. OC187 strain and which lacks activity of forming L-4-hydroxy-2-ketoglutaric acid.

*Bacillus* sp. OC187 has been newly isolated by the present inventors from soil in Machida city, Tokyo, Japan. The bacteriological properties of the strain are shown in Tables 1—1 to 1–6 below.

TABLE 1-1

| Morphological properties | |
|---|---|
| Cell morphology | rod |
| Cell size | 0.8–1.0 × 3.0–4.0 μm |
| Cell polymorphism | not observed |
| Cell motility | observed |
| Position of flagella | peripheral |
| Spore | observed |
| Spore morphology | ellipse |
| Position of spore | central |

TABLE 1-2

| Cultural characteristics in various media | | |
|---|---|---|
| Bouillon-agar medium (Meat extract) | growth | good |
| | surface | smooth |
| | color | light pink |
| | gloss | none |
| | diffusible pigments | negative |
| Bouillon-liquid medium (Meat extract) | surface growth | not observed |
| | turbidity | positive |
| Bouillon-gelatin medium Liquefaction of gelatin | | negative |
| Litmus milk | reaction | acid |
| | coagulation | positive |
| | liquefaction | negative |

TABLE 1-3

| Physiological properties — 1 | |
|---|---|
| 1. Gram staining | + or − |
| 2. Reduction to nitrate salt | − |
| 3. Denitrification reaction | + |
| 4. Methyl red test | − |
| 5. VP test | + |
| 6. Indole production | − |
| 7. Hydrogen sulfide production | − |
| 8. Utilization of citric acid | |
| Koser's method | + |
| Christensen's method | + |
| 9. Utilization of inorganic nitrogen source | |
| Nitrates | + |
| Ammonium salts | + |
| 10. Pigment production | |
| King A medium | − |
| King B medium | − |
| 11. Urease | + |
| 12. Oxidase | − |
| 13. Catalase | + |
| 14. Growth range | |
| pH | 5.2–9.7 |
| (Optimum pH) | (approximately 7.0) |
| Temperature | 15–56° C. |
| (Optimum temperature) | (approximately 47° C.) |
| 15. Attitude toward oxygen | |
| Aerobic | + |
| Anaerobic (facultative anaerobic) | + |
| 16. OF test | fermentative |

+: Positive, −: Negative

TABLE 1-4

Physiological properties — 2

| Production of acid and gas | Conditions | | | |
|---|---|---|---|---|
| | Aerobic | | Anaerobic | |
| (Day 6) | Acid | Gas | Acid | Gas |
| 1. L-Arabinose | + | − | + | − |
| 2. D-Xylose | + | − | − | − |
| 3. D-Glucose | + | − | + | − |
| 4. D-Mannose | + | − | + | − |
| 5. D-Fructose | + | − | + | − |
| 6. D-Galactose | + | − | − | − |
| 7. Maltose | + | − | + | − |
| 8. Sucrose | + | − | + | − |
| 9. Lactose | − | − | − | − |
| 10. Trehalose | + | − | + | − |
| 11. D-Sorbitol | − | − | − | − |
| 12. D-Mannitol | + | − | + | − |
| 13. Inositol | − | − | − | − |
| 14. Glycerol | + | − | − | − |
| 15. Starch | + | − | + | − |

+: Positive, −: Negative

TABLE 1-5

Other properties

| | |
|---|---|
| 1. Degradation of esculin | + |
| 2. Degradation of malonic acid | − |
| 3. Degradation of arginine | + |
| 4. Decarboxylation of lysine | − |
| 5. Decarboxylation of ornithine | − |
| 6. Deamination of phenylalanine | − |
| 7. Resistance to sodium chloride | viable at 10% |

+: Positive, −: Negative

TABLE 1-6

Chemotaxonomic properties

| | |
|---|---|
| 1. Base composition of DNA (G + C mol %) | 45.9 |
| 2. Cellular lipid:major quinone | MK-7 |
| 3. Diamino acid composition of cell wall peptidoglycan | meso-$A_2$ pm |

The strain having the bacteriological properties mentioned above was classified according to Bergey's Manual of Systematic Bacteriology, vol. 2 (1986). As a result, the strain was classified to the genus *Bacillus* and was designated as *Bacillus* sp. OC187.

*Bacillus* sp. OC187 and *Bacillus* sp. S16 were deposited with the National Institute of Bioscience and Human Technology, Agency of Industrial Science and Technology, Japan, on Apr. 19, 1994 as FERM BP-4646 and FERM BP-4647, respectively, under the Budapest Treaty.

For producing L-4-hydroxy-2-ketoglutaric acid, microorganisms of the genus *Pseudomonas, Paracoccus, Providencia, Rhizobium* or *Morganella* are especially preferable. Specifically, those further having activity of forming L-4-hydroxy-2-ketoglutaric acid from pyruvic acid or a compound capable of being converted into pyruvic acid by the microorganisms and glyoxylic acid are preferably employed. More preferable are those which do not substantially produce D-4-hydroxy-2-ketoglutaric acid.

Specific examples of the microorganisms include *Pseudomonas putida* ATCC 795, *Pseudomonas putida* ATCC 4359, *Pseudomonas saccharophila* ATCC 9114 (=ATCC 15946; IAM Catalogue of Strains (1993)], *Pseudomonas boreopolis* ATCC 15452, *Pseudomonas taetrolens* ATCC 17466, *Pseudomonas oleovorans* ATCC 8062, *Paracoccus denitrificans* ATCC 19367, *Providencia rustigianii* ATCC 13159, *Rhizobium meliloti* RCR 2001 (FERM BP-4582), and *Morganella morganii* ATCC 25830.

*Rhizobium meliloti* RCR 2001 was deposited with the National Institute of Bioscience and Human Technology, Agency of Industrial Science and Technology, Japan, on Feb. 24, 1994 as FERM BP-4582, under the Budapest Treaty.

The microorganism used as biocatalyst III is cultivated by a conventional method.

The medium for cultivating these microorganisms may be any of a natural medium and a synthetic medium so long as it contains a carbon source, a nitrogen source, an inorganic salt, and the like, that may be assimilated by the microorganisms used.

Any carbon source can be employed so long as it can be assimilated by the microorganism. Examples of the carbon source include sugars such as glucose, fructose, sucrose, maltose, starch, starch hydrolysates and molasses; organic acids such as acetic acid, lactic acid and gluconic acid; and alcohols such as ethanol and propanol. When D-4-hydroxy-2-ketoglutaric acid is produced using a bacterium of the genus *Cellvibrio* or *Bacillus*, D-galactonic acid is preferable as the carbon source.

Any nitrogen source can be employed so long as it can be assimilated by the microorganism. Examples of the nitrogen source include ammonia, ammonium salts of inorganic and organic acids such as ammonium sulfate, ammonium chloride, ammonium acetate and ammonium phosphate, other nitrogen-containing compounds, peptone, meat extract, yeast extract, corn steep liquor, casein hydrolysates, soybean cake, soybean cake hydrolysates, fermented strains, and digested products thereof.

Any inorganic salt can be employed so long as it can be assimilated by the microorganism used. Examples of the inorganic salt include potassium dihydrogen phosphate, dipotassium hydrogen phosphate, ammonium sulfate, ammonium chloride, sodium chloride, magnesium sulfate, ferrous sulfate and manganese sulfate. In addition, trace elements such as calcium, zinc, boron, copper, cobalt and molybdenum may be added to the culture medium. Further, vitamins such as thiamine and biotin, amino acids such as glutamic acid and aspartic acid, and nucleic acid-related compounds such as adenine and guanine may be added to the culture medium, if necessary.

The cultivation of these microorganism is carried out under aerobic conditions such as shaking-culture and submerged aerial stirring culture. It is advisable that the cultivation be carried out at a temperature of 15° to 37° C. for 10 to 96 hours.

During the cultivation, the pH of the culture is maintained at 5.0 to 9.0. The pH is adjusted with an inorganic or organic acid, alkaline solution, urea, calcium carbonate or ammonia.

The processed cells of the microorganism used as biocatalyst III include a dried cells, lyophilized cells, surfactant- or organic solvent-treated cells, enzymatically-treated cells, ultrasonically-treated cells, mechanically-compressed cells, cellular protein fraction, and immobilized product of unprocessed cells or processed cells.

Examples of the aqueous medium include water; buffers such as a phosphate buffer, carbonate buffer, acetate buffer, borate buffer, citrate buffer and tris buffer; and aqueous solutions containing organic solvents, for example, alcohols such as methanol and ethanol, esters such as ethyl acetate, ketones such as acetone and amides such as acetamide. If necessary, a surfactant such as Triton X-100 (made by Nacalai Tesque, Inc.) and Nonion HS204 (made by Nippon Oil & Fats Co., Ltd.) or an organic solvent such as toluene or xylene may be added to the aqueous medium at the concentration of approximately 0.1 to 20 g/liter.

The concentration of pyruvic acid or glyoxylic acid used is 1 to 200 g/liter, preferably 20 to 200 g/liter. The compound capable of being converted into pyruvic acid by biocatalyst III can replace pyruvic acid. Examples of such a compound include sugars such as glucose, fructose, sucrose, maltose, starch, starch hydrolysates and molasses; and organic acids such as acetic acid, lactic acid and gluconic acid.

The concentration of biocatalyst III is 0.1 to 200 g/liter, preferably 5 to 100 g/liter (calculated in terms of the cells of the microorganism).

The optically active 4-hydroxy-2-ketoglutaric acid can be produced by adding biocatalyst III, pyruvic acid and glyoxylic acid at the above-mentioned concentrations to the aqueous medium, and reacting the mixture at a temperature of 15° to 60° C., preferably 25° to 45° C. for 30 minutes to 80 hours at a pH of 3 to 11, preferably 5 to 9.

The optically active 4-hydroxy-2-ketoglutaric acid can be also produced by adding pyruvic acid and glyoxylic acid at the above-mentioned concentrations to the aqueous medium at the starting point of, or during, the culturing of the microorganism used as biocatalyst III.

The optically active 4-hydroxy-2-ketoglutaric acid can be isolated by a conventional method of purifying amino acids. For instance, the optically active 4-hydroxy-2-ketoglutaric acid can be isolated from the supernatant of the reaction solution from which the solids are removed by centrifugation through a combination of treatment with an ion exchange resin, membrane, and the like.

EXAMPLES

The present invention will be illustrated specifically by referring to the following Examples.

EXAMPLE 1

A medium containing 10 g/liter bactotryptone, 5 g/liter yeast extract and 5 g/liter sodium chloride and being adjusted to a pH of 7 with NaOH (L medium) was put in test tubes in an amount of 3 ml each, and the test tubes were sterilized. Then, microorganisms shown in Table 2 were inoculated thereon, and cultivated at 30° C. for 16 hours by shaking culture. One milliliter of the culture for each of the microorganisms was inoculated into a sterilized test tube filled with 10 ml of the GMG medium having the following composition, and was cultivated at 30° C. for 20 hours by shaking culture.

Composition of GMG medium (amounts per liter):

| | |
|---|---|
| $KH_2PO_4$ | 2 g |
| $(NH_4)_2SO_4$ | 2 g |
| $FeSO_4 \cdot 7H_2O$ | 5 mg |
| $MnSO_4 \cdot 7H_2O$ | 2 mg |
| $MgSO_4 \cdot 7H_2O$ | 0.5 g |
| $CaCl_2$ | 10 mg |
| Yeast extract | 1 g |
| Peptone | 1 g |
| Glucose | 20 g |
| pH | 7.0 |

After the completion of the cultivation, the cells were collected by centrifugation, and resuspended in 1 ml of a sterilized reaction solution (a) [a solution containing 3 g of $KH_2PO_4$, 6 g of $NaH_2PO_4$, 1 g of $NH_4Cl$, 0.16 g of $MgSO_4 \cdot 7H_2O$, 5 g of NaCl, 11 mg of $CaCl_2$, 100 mmols of sodium pyruvate and 100 mmols of glyoxylic acid in 1 liter of purified water and being adjusted to pH 7.0 with NaOH]. The suspension was shaken in a 2059 tube (manufactured by Falcon Co.) at 30° C. for 5 hours. After the completion of the reaction, the cells were removed from the suspension by centrifugation, and the amount of γ-hydroxy-L-glutamic acid in the supernatant was determined by HPLC using an ODS column (manufactured by Merck). The results are shown in Table 2. In the determination, standard compounds for threo- and erythro-γ-hydroxy-L-glutamic acids were prepared by the methods described in Journal of American Chemical Society (J.A.C.S.), 79, 6192 (1957)].

TABLE 2

| | Yield of γ-hydroxy-L-glutamic acid (mM) | |
|---|---|---|
| Strains | Threo-form | Erythro-form |
| Pseudomonas putida ATCC 795 | 2.1 | 0.0 |
| Pseudomonas putida ATCC 4359 | 1.0 | 0.0 |
| Pseudomonas oleovorans ATCC 8062 | 1.1 | 0.0 |
| Pseudomonas saccharophila ATCC 15946 | 1.4 | 0.0 |
| Pseudomonas boreopolis ATCC 15452 | 0.5 | 0.0 |
| Pseudomonas taetorolens ATCC 17466 | 1.2 | 0.0 |
| Paracoccus denitrificans ATCC 19367 | 1.3 | 0.0 |
| Providencia rustigianii ATCC 13159 | 1.3 | 0.0 |
| Rhizobium meliloti FERM BP-4582 | 0.6 | 0.0 |
| Morganella morganii ATCC 25830 | 0.3 | 0.0 |
| Enterobacter aerogenes ATCC 13048 | 0.5 | 0.0 |
| Arthrobacter crystallopoietes ATCC 15482 | 0.4 | 0.0 |
| Caulobacter crescentus ATCC 19089 | 0.4 | 0.0 |
| Microbacterium imperiale ATCC 8365 | 0.4 | 0.0 |
| Brevibacterium citreum ATCC 15828 | 0.1 | 0.0 |
| Brevibacterium ammoniagenes ATCC 6871 | 0.1 | 0.0 |
| Corynebacterium michiganense ATCC 10202 | 0.1 | 0.0 |
| Clavibacter rathayi ATCC 13659 | 0.1 | 0.0 |
| Clavibacter tritici ATCC 11402 | 0.1 | 0.0 |

EXAMPLE 2

The same procedure described in Example 1 was repeated except that the microorganisms shown in Table 8 was employed and a reaction solution obtained by adding 5 g/liter of aspartic acid to reaction solution (a) was used. After the completion of the reaction, the amount of γ-hydroxy-L-glutamic acid in the supernatant of the reaction solution was determined in the same manner as in Example 1. The results are shown in Table 3.

TABLE 3

| | Yield of γ-hydroxy-L-glutamic acid (mM) | |
|---|---|---|
| Strains | Threo-form | Erythro-form |
| Pseudomonas putida ATCC 795 | 7.2 | 0.0 |
| Pseudomonas saccharophila ATCC 15946 | 6.0 | 0.0 |
| Paracoccus denitrificans ATCC 19367 | 5.3 | 0.0 |
| Providencia rustigianii ATCC 13159 | 5.3 | 0.0 |
| Morganella morganii ATCC 25830 | 2.4 | 0.0 |

EXAMPLE 3

E. coli ATCC 33625, which is a sub-strain of E. coli K-12, and E. coli HKK2 (sucA, iclR, trp) deprived of α-ketoglutaric acid dehydrogenase activity were cultured in a test tube filled with 3 ml of L medium overnight at 37° C. Two milliliter of the culture was put into a 300-milliliter conical flask filled with 50 ml of M9 medium [a medium obtained by adjusting the pH of the medium containing 6 g of $Na_2HPO_4$, 3 g of $KH_2PO_4$, 0.5 g of NaCl and 1 g of $NH_4Cl$ in 1 liter of purified water to pH 7.4 and adding 2 ml of sterilized 1M $MgSO_4$ and 0.1 ml of sterilized 1M $CaCl_2$] further containing 0.4% glucose, 0.05% succinic acid, 0.2% ammonium sulfate, 100 mg/liter of L-tryptophan, 0.1% yeast extract and 0.1% peptone, and cultivated at 37° C. for 8 hours. The supernatant was removed from the obtained culture by centrifugation, and the cells were suspended in sterilized water such that the concentration of the wet cells was reached 100 g/liter.

On the other hand, *Pseudomonas saccharophila* ATCC 15946 was cultivated in three test tubes each filled with 10 ml of GMS medium at 30° C. for 20 hours in the same manner as in Example 1. The cells in these three test tubes were collected by centrifugation, and then suspended in 3 ml of a reaction mixture. The reaction was conducted at 30° C. for 5 hours. The reaction mixture was centrifuged to obtain a supernatant. The supernatant was analyzed by HPLC using a SUMICHIRAL OA-5000 column (manufactured by Sumitomo Chemical Co., Ltd.). As a result, it was found that 60.5 mM of L-4-hydroxy-2-ketoglutaric acid was formed in the supernatant. D-4-hydroxy-2-ketoglutaric acid was not detected. Standard compounds for D- and L-4-hydroxy-2-ketoglutaric acids were prepared by the method described in Methods in Enzymology, 17, part B, 275.

This supernatant was put into two 2059 tubes (manufactured by Falcon Co.) in an amount of 0.4 ml each, and the above-obtained suspension of E. coli strain was added thereto in an amount of 80 µl each. Further, 40 µl of a 20% ammonium sulfate solution, 48 µl of a 50% glucose solution and 80 µl of M9C solution (a solution containing 60 g of $Na_2HPO_4$, 30 g of $KH_2PO_4$, 5 g of NaCl and 10 g of $NH_4Cl$ in 1 liter of purified water, pH 7.4) were added to each of the two test tubes, and the total amount of the mixture was adjusted to 0.8 ml with sterilized water. The mixture was reacted at 37° C. for 3 hours with shaking. After the completion of the reaction, the cells were removed by centrifugation, and γ-hydroxy-L-glutamic acid in the supernatant was determined by HPLC in the same manner as in Example 1. The results are shown in Table 4.

TABLE 4

| Strains | Yield of γ-hydroxy-L-glutamic acid (mM) | |
|---|---|---|
| | Threo-form | Erythro-form |
| E. coli ATCC 33625 | 5.4 | 0.0 |
| E. coli HKK2 | 9.6 | 0.0 |
| E. coli HKK2/pHK10 | 19.8 | 0.0 |
| E. coli HKK27/pHK10 | 29.8 | 0.0 |

EXAMPLE 4

A mutant having decreased L-4-hydroxy-2-ketoglutaric acid degrading activity was derived from α-ketoglutaric acid dehydrogenase activity-deficient mutant E. coli HKK2 (sucA, iclR, trp) of E. coli K-12. E. coli HKK2 was cultivated in L medium until the logarithmic growth phase. The cells of E. coli HKK2 were collected, washed with 0.05 M tris-maleate buffer (pH 6.0), and then suspended in the same buffer such that the concentration of the cells became approximately $10^9$ cells/ml. NTG was added to the suspension such that the final concentration became 600 mg/liter, and the mixture was kept at room temperature for 20 minutes to mutagenize the cells. The mutagenized cells were spreaded onto L agar medium (a medium obtained by adding 2% agar to L medium). Approximately 3,000 colonies thus obtained were measured with respect to L-4-hydroxy-2-ketoglutaric acid degrading activity. The colonies were cultivated in 3 ml of L medium at 37° C. for 16 hours. The cells were then collected by centrifugation, and suspended in 0.5 ml of 50 mM $KH_2PO_4$ (pH 7) buffer. To the suspension was added 0.5 ml of a broth containing L-4-hydroxy-2-ketoglutaric acid obtained using *Pseudomonas saccharophila* ATCC 15946 in the same manner as in Example 3. The mixture was incubated at 37° C. for 8 hours. The concentrations of 4-hydroxy-2-ketoglutaric acid before and after the incubation were measured in the same manner as in Example 3, and the strain containing 4-hydroxy-2-ketoglutaric acid in the mixture was selected as the strain having decreased L-4-hydroxy-2-ketoglutaric acid degrading activity. Thus, E. coli HKK27 having deficiency of α-ketoglutaric acid hydrogenase activity and decreased L-4-hydroxy-2-ketoglutaric acid degrading activity was obtained. The strain having deficiency of α-ketoglutaric acid hydrogenase activity and decreased L-4-hydroxy-2-ketoglutaric acid degrading activity can be also obtained by deriving the mutant having decreased D-4-hydroxy-2-ketoglutaric acid degrading activity from E. coli HKK2 according to the above-mentioned method.

EXAMPLE 5

A glutamic acid dehydrogenase gene was isolated from E. coli ATCC 33625, which is a sub-strain of E. coli K-12, by a conventional method [Biochim. Biophys. Acta, 72, 619 (1963)]. pBR322 used as a vector was a product of Takara Shuzo Co., Ltd. Sixteen units of each of PstI and ClaI (both manufactured by Takara Shuzo Co., Ltd.) were added to 100 µl of a restriction endonuclease reaction mixture containing 1 µg of pBR322 plasmid DNA and 3 µg of chromosomal DNA of ATCC 33625 (H buffer manufactured by Takara Shuzo Co., Ltd.), and the mixture was reacted at 37° C. for 2 hours. Subsequently, the reaction mixture was heated at 65° C. for 40 minutes to stop the reaction. To the reaction mixture were added 12 µl of T4 ligase buffer (a buffer containing 600 mM tris, 66 mM $MgCl_2$, and 100 mM dithiothreitol, pH 7.6) having a concentration of 10 times, 3 µl of 100 mM ATP and 350 units of T4 ligase (manufactured by Takara Shuzo Co., Ltd.), and the mixture was reacted at 15° C. for 16 hours. The ligase reaction product was used to transform PA340 strain [J. Bacteriol., 133, 139 (1978)] deprived of both of glutamic acid dehydrogenase activity and glutamic acid synthetase activity [Maniatis, et al., Molecular Cloning, A Laboratory Manual, 250 (1982)]. M9 minimum agar medium containing 25 mg/liter L-threonine, 25 mg/liter L-leucine, 25 mg/liter L-histidine, 25 mg/liter L-arginine, 100 µg/liter thiamine, 10 mg/liter tetracycline and 0.4% glucose [Maniatis, et al., Molecular Cloning, A Laboratory Manual, 68 (1982)] was used as a screening medium. From the cultured cells of the transformant, the plasmid DNA was isolated by the method described in Maniatis, et al. [Molecular Cloning, A Laboratory Manual, 86 (1982)].

The plasmid which was obtained from one transformant and named pHK10 was analyzed by digestion with restriction endonucleases and agarose gel electrophoresis. Consequently, it was observed that in this plasmid, a PstI-ClaI DNA fragment of approximately 4.2 kb having the same structure as the glutamic acid dehydrogenase gene reported by MacFarson, et al. [Nucleic Acid Res., 11, 5257 (1983)] was inserted between PstI site and ClaI site of pBR322. PA340 strain was retransformed with pHK10. L-agar medium containing 10 mg/liter tetracycline was used as a screening medium. The 50 tetracycline-resistant transformant colonies obtained were optionally selected, and replicated in M9 minimum agar medium containing 25 mg/liter L-threonine, 25 mg/liter L-leucine, 25 mg/liter L-histidine, 25 mg/liter L-arginine, 100 µg/liter thiamine, 10 mg/liter tetracycline and 0.4% glucose. As a result, all of the colonies were grown. Further, with respect to the obtained retransformant and PA340 strain used as a host, glutamic acid dehydrogenase activity was measured according to the method described by Sakamoto, et al. [Journal of Biotechnology, 124, 775 (1975)]. Consequently, the above-mentioned activity was not observed in PA340 strain, whereas the activity was clearly observed in PA340 strain containing pHK10. The result proved that the glutamic acid dehydrogenase gene of E. coli ATCC 33625, which is a sub-strain of E- coli K-12 strain, was cloned.

EXAMPLE 6

The glutamic acid dehydrogenase gene-containing plasmid pHK10 obtained in Example 5 was transformed with E. coli HKK2 and E. coli HKK27 formed in Example 4 by the conventional method [Maniatis, et al., Molecular Cloning, A Laboratory Manual, 68 (1982)] to obtain E. coli HKK2/pHK10 and E. coli HKK27/pHK10. These transformants were cultivated in the same manner as in Example 3. The cultivation of these transformants was carried out by adding 10 mg/liter tetracycline to either test tubes or conical flasks. From the obtained culture, the supernatant was removed by centrifugation, and the cells were suspended in sterilized water such that the concentration of the wet cells reached 100 g/liter. On the other hand, a supernatant of a broth containing 59.9 mM of L-4-hydroxy-2-ketoglutaric acid prepared using Pseudomonas saccharophila ATCC 15946 in the same manner as in Example 3 was put into two 2059 tubes (manufactured by Falcon Co.) in an amount of 0.4 ml each. The E. coli strain suspension prepared above was added thereto in an amount of 80 µl each. Further, 40 µl of a 20% ammonium sulfate solution, 48 µl of a 50% glucose solution and 80 µl of M9C solution were added to each of the tubes. The total amount of the mixture was adjusted to 0.8 ml with sterilized water, and the mixture was reacted at 37° C. for 3 hours with shaking. After the completion of the reaction, the cells were removed by centrifugation, and the amount of γ-hydroxy-L-glutamic acid in the supernatant was determined by HPLC in the same manner as in Example 1. The results are shown in Table 4 (refer to Example 3).

EXAMPLE 7

Each of the microorganisms shown in Table 5 was cultivated in the same manner as in Example 1, and suspended in 1 ml of a reaction mixture. The reaction was conducted at 30° C. for 5 hours. The amount of 4-hydroxy-2-ketoglutaric acid (abbreviated as "KHG" in Table 5) formed in the reaction solution was determined in the same manner as in Example 3. The results are shown in Table 5. Further, the reaction solution was centrifuged to obtain a supernatant. To 0.4 ml of the supernatant were added a suspension of E. coli HKK27/pHK10, glucose, ammonium sulfate and M9C solution as in Example 6. The total amount of the mixture was adjusted to 0.8 ml with sterilized water, and the mixture was reacted at 37° C. for 3 hours with shaking. After the completion of the reaction, the cells were removed by centrifugation, and the amount of γ-hydroxy-L-glutamic acid in the supernatant (abbreviated as "HG" in Table 5) was determined by HPLC. The results are shown in Table 5.

TABLE 5

| | Yield (mM) | | | |
|---|---|---|---|---|
| | KHG | | HG | |
| Strains | L-form | D-form | Threo-form | Erythro-form |
| Pseudomonas putida ATCC 795 | 61.3 | 0.0 | 19.8 | 0.0 |
| Pseudomonas putida ATCC 4359 | 29.8 | 0.0 | 10.4 | 0.0 |
| Pseudomonas oleovorans ATCC 8062 | 33.0 | 0.0 | 11.6 | 0.0 |
| Pseudomonas saccharophila ATCC 15946 | 40.5 | 0.0 | 14.2 | 0.0 |
| Pseudomonas boreopolis ATCC 15452 | 14.9 | 0.0 | 5.2 | 0.0 |
| Pseudomonas taetorolens ATCC 17466 | 35.0 | 0.0 | 12.3 | 0.0 |
| Paracoccus denitrificans ATCC 19367 | 40.0 | 0.0 | 13.8 | 0.0 |
| Providencia rustigianii ATCC 13159 | 40.0 | 0.0 | 14.0 | 0.0 |
| Rhizobium meliloti FERM BP-4582 | 15.7 | 0.0 | 5.5 | 0.0 |
| Morganella morganii ATCC 25830 | 10.0 | 0.0 | 3.5 | 0.0 |

EXAMPLE 8

In the same manner as in Example 1, cells of Pseudomonas saccharophila ATCC 15946 were put into 10 test tubes each filled with 10 ml of GMS medium, and cultivated at 30° C. for 20 hours. The cells in these 10 test tubes were collected by centrifugation, suspended in 10 ml of a reaction solution, and reacted at 30° C. for 5 hours. This reaction mixture was centrifuged to obtain a supernatant. The obtained supernatant was analyzed by HPLC using a SUMICHIRAL OA-5000 column (manufactured by Sumitomo Chemical Co., Ltd.). It was found that 68.8 mM of L-4-hydroxy-2-ketoglutaric acid was formed. D-4-hydroxy-2-ketoglutaric acid was not detected.

This supernatant was put into 4 sterilized thick test tubes in an amount of 2.5 ml each. MSC medium (0.5 ml) having the composition mentioned below, 0.5 ml of a 50% glucose solution and 1 ml of a 10% ammonium chloride solution were sterilized and added to each of the test tubes. Further, 0.5 ml of a culture of Arthrobacter protophomiae ATCC 19271 which was cultivated in a test tube containing 3 ml of L medium overnight at 30° C. was added to one of the above-mentioned test tubes, 0.5 ml of a culture solution of Pseudomonas chlororaphis ATCC 9446 which was cultivated in the same manner was added to one of the test tubes, 0.5 ml of a culture of Serratia marcesens ATCC 13880 which was cultivated in the same manner was added to one of the test tubes, and 0.5 ml of a culture of Corynebacterium glutamicum ATCC 13032 which was cultivated in the same manner was added to one of the test tubes, respectively. These were cultivated at 30° C. for 48 hours. After the completion of the cultivation, the cells were removed by centrifugation, and the amount of γ-hydroxy-L-glutamic acid in the supernatant was determined by HPLC in the same manner as in Example 1. The results are shown in Table 6.

Composition of MSC medium (amounts per liter):

| | |
|---|---|
| $KH_2PO_4$ | 20 g |
| $(NH_4)_2SO_4$ | 20 g |
| $FeSO_4.7H_2O$ | 50 mg |
| $MnSO_4.7H_2O$ | 20 mg |
| $MgSO_4.7H_2O$ | 5 g |
| $CaCl_2$ | 100 mg |
| Yeast extract | 10 g |
| Peptone | 10 g |
| pH | 7.0 |

TABLE 6

| | Yield of γ-hydroxy-L-glutamic acid (mM) | |
|---|---|---|
| Strains | Threo-form | Erythro-form |
| *Arthrobacter protophomiae* ATCC 19271 | 7.2 | 0.0 |
| *Pseudomonas chlororaphis* ATCC 9446 | 13.1 | 0.0 |
| *Serratia marcesens* ATCC 13880 | 10.2 | 0.0 |
| *Corynebacterium glutamicum* ATCC 13032 | 6.2 | 0.0 |

EXAMPLE 9

*Pseudomonas saccharophila* ATCC 15946 was inoculated in 9 ml of L medium, and cultivated at 30° C. for 16 hours with shaking. The whole amount of the culture was inoculated in 300 ml of GMS medium, and cultivated in a 2-liter conical flask at 30° C. for 20 hours with shaking. The cells were collected from the obtained culture by centrifugation, and suspended in 60 ml of the same reaction mixture as that used in Example 1. The reaction was carried out in a 300-milliliter beaker with stirring. After 6 hours from the starting point of the reaction, 3 ml of a 2M sodium pyruvate solution and 3 ml of a 2M sodium glyoxylate solution were added thereto. After 24 hours from the starting point of the reaction, the cells were removed from the reaction mixture by centrifugation to obtain the supernatant of the first reaction mixture.

Meanwhile, E. coli HKK27/pHK10 was cultivated overnight at 37° C. in 10 ml of L medium containing 10 mg/liter tetracycline. The whole amount of the culture was added to a 2-liter conical flask containing 750 ml of M9 medium supplemented with 0.4% glucose, 0.05% succinic acid, 0.2% ammonium sulfate, 100 mg/liter L-tryptophan, 0.1% yeast extract, 0.1% peptone and 10 mg/liter tetracycline, and the mixture was cultivated at 37° C. for 8 hours. From the obtained culture, the supernatant was removed by centrifugation, and the cells were suspended in sterilized water such that the concentration of the wet cells reached 100 g/liter.

Eight milliliter of the above-obtained E. coli HKK27/pHK10 suspension, 4.8 ml of a 50% glucose solution, 4 ml of a 20% ammonium sulfate solution, 8 ml of M9C solution and 5.2 ml of sterilized water were added to 50 ml of the above-obtained first reaction mixture. The second reaction was carried out in a 300-milliliter beaker with stirring. During the second reaction, the pH was maintained at 7 with 7% aqueous ammonia. After 12 hours from the starting point of the reaction, the cells were removed by centrifugation, and the amount of γ-hydroxy-L-glutamic acid in the supernatant was determined by HPLC using an ODS column (manufactured by Merck). As a result, 10.3 g/liter of threo-γ-hydroxy-L-glutamic acid was detected.

EXAMPLE 10

The supernatant (75 ml) of the second reaction mixture obtained in Example 9 was passed through a column of a strongly acidic cation exchange resin [DoweX 50×8 (Na-type), manufactured by Dow Chemical Company]. Threo-γ-hydroxy-L-glutamic acid was eluted with ammonia, concentrated and crystallized to obtain 0.6 g of threo-γ-hydroxy-L-glutamic acid crystals.

EXAMPLE 11

L medium containing 10 g/liter bactopeptone, 5 g/liter yeast extract and 5 g/liter sodium chloride and being adjusted to a pH of 7 with NaOH was put in test tubes in an amount of 3 ml each. After the test tubes were sterilized, *Bacillus* sp. S16 (FERM BP-4647) was inoculated into the medium, and cultured at 30° C. for 16 hours with shaking. The culture was inoculated into two sterilized test tubes each filled with 10 ml of GMSG medium having the following composition in an amount of 1 ml each, and was cultivated at 30° C. for 20 hours with shaking.

Composition of GMSG medium (amounts per liter):

| | |
|---|---|
| $KH_2PO_4$ | 2 g |
| $(NH_4)_2SO_4$ | 2 g |
| $FeSO_4.7H_2O$ | 5 mg |
| $MnSO_4.7H_2O$ | 2 mg |
| $MgSO_4.7H_2O$ | 0.5 g |
| $CaCl_2$ | 10 mg |
| Yeast extract | 1 g |
| Peptone | 1 g |
| Calcium D-galactonate | 20 g |
| pH | 7.0 |

After the completion of the cultivation, the cells were collected by centrifugation and suspended in 1 ml of a reaction mixture obtained by adding aspartic acid at the concentration of 5 g/liter to 1 ml of the sterilized reaction mixture (a). The reaction was carried out in a 2059 tube (manufactured by Falcon Co.) at 30° C. for 5 hours with shaking. After the completion of the reaction, the cells were removed by centrifugation, and the amount of γ-hydroxy-L-glutamic acid in the supernatant was determined in the same manner as in Example 1. The results are shown in Table 7.

TABLE 7

| | Yield of γ-hydroxy-L-glutamic acid (mM) | |
|---|---|---|
| Reaction mixture | Threo-form | Erythro-form |
| (a) | 0.0 | 1.3 |
| (a) + aspartic acid | 0.0 | 4.6 |

EXAMPLE 12

E. coli ATCC 33625 derived from E. coli K-12 and mutant E- coli HKK2 (sucA, iclR, trp) deprived of α-ketoglutaric acid dehydrogenase activity were cultivated in a test tube containing 3 ml of L medium overnight at 37° C. Two milliliter of the culture solution was added to a 300-milliliter conical flask filled with 50 ml of M9 medium supplemented with 0.4% glucose, 0.05% succinic acid, 0.2% ammonium sulfate, 100 mg/liter L-tryptophan, 0.1% yeast extract and 0.1% peptone, and the mixture was cultivated at 37° C. for 8 hours. From the obtained culture, the supernatant was removed by centrifugation, and the cells were suspended in sterilized water such that the concentration of the wet cells reached 100 g/liter.

Meanwhile, in the same manner as in Example 11, cells of Bacillus ep. S16 (FERM BP-4647) were put into three test tubes each filled with 10 ml of GMSG medium, and the cultivation was carried out at 30° C. for 20 hours. The cells of these three test tubes were collected by centrifugation, and then suspended in 3 ml of the reaction mixture (a). The reaction was carried out at 30° C. for 5 hours. The reaction mixture was centrifuged to obtain a supernatant. The supernatant was analyzed by HPLC using a SUMICHIRAL DA-5000 column (manufactured by Sumitomo Chemical Co., Ltd.). As a result, it was found that 39.0 mM of D-4-hydroxy-2-ketoglutaric acid was formed. L-4-hydroxy-2-ketoglutaric acid was not detected. Standard compounds for D- and L-4-hydroxy-2-ketoglutaric acids were prepared by the method described in Methods in Enzymology, 17, part B, 275.

This supernatant was put into two 2059 tubes (manufactured by Falcon Co.) in an amount of 0.4 ml each. The above-obtained E. coli strain suspension was added thereto in an amount of 80 µl each. Further, 40 µl of a 20% ammonium sulfate solution, 48 µl of a 50% glucose solution and 80 µl of M9C solution were added to each of the two tubes, and the total amount of the mixture was adjusted to 0.8 ml with sterilized water. The mixture was reacted at 37° C. for 3 hours with shaking. After the completion of the reaction, the cells were removed by centrifugation, and the amount of γ-hydroxy-L-glutamic acid in the supernatant was determined by HPLC in the same manner as in Example 1. The results are shown in Table 8.

TABLE 8

| Strains | Yield of γ-hydroxy-L-glutamic acid (mM) | |
|---|---|---|
| | Threo-form | Erythro-form |
| E. coli ATCC 33625 | 0.0 | 4.9 |
| E. coli HKK2 | 0.0 | 7.8 |
| E. coli HKK2/pHK10 | 0.0 | 13.4 |
| E. coli HKK27/pHK10 | 0.0 | 16.5 |

EXAMPLE 13

E. coli HKK2/pHK10 strain and E. coli HKK27/pHK10 strain were cultivated in the same manner as in Example 12. The transformants were cultivated in either test tubes or conical flasks with the addition of 10 mg/liter of tetracycline. From the obtained culture, the supernatant was removed by centrifugation, and suspended in sterile water such that the concentration of the wet cells reached 100 g/liter.

On the other hand, a supernatant of a broth containing 38.8 mM of D-4-hydroxy-2-ketoglutaric acid prepared using Bacillus ep. S16 (FERM BP-4647) in the same manner as in Example 12 was put into two 2059 tubes (manufactured by Falcon Co.) in an amount of 0.4 ml each, and the above-obtained E. coli strain suspension was further added thereto in an amount of 80 µl each. Moreover, 40 µl of a 20% ammonium sulfate solution, 48 µl of a 50% glucose solution and 80 µl of M9C solution were added to each of the two tubes. The total amount of the mixture was adjusted to 0.8 ml with sterilized water. The reaction was conducted at 37° C. for 3 hours with shaking. After the completion of the reaction, the cells were removed by centrifugation, and the amount of γ-hydroxy-L-glutamic acid in the supernatant was determined by HPLC in the same manner as in Example 1. The results are shown in Table 8 (refer to Example 12).

EXAMPLE 14

Bacillus sp. OC187 (FERM BP-4646) was cultivated in the same manner as in Example 11. After the completion of the cultivation, the culture solution in one test tube was heated at 80° C. for 1 hour, and the culture in another test tube was maintained at 30° C. The cells in each test tubes were then collected by centrifugation, and suspended in 1 ml of the reaction mixture (a). The reaction was carried out at 30° C. for 5 hours. The amount of 4-hydroxy-2-ketoglutaric acid (abbreviated as "KHG" in Table 9) formed in the reaction mixture was determined in the same manner as in Example 12. The results are shown in Table 9. The reaction mixture was centrifuged to obtain a supernatant. To 0.4 ml of the supernatant were added the HKK27/pHK10 strain suspension, glucose, ammonium sulfate and M9C solution in the same manner as in Example 13. The total amount of the mixture was adjusted to 0.8 ml with sterilized water. The reaction was carried out at 37° C. for 3 hours with shaking. After the completion of the reaction, the cells were removed by centrifugation, and the amount of γ-hydroxy-L-glutamic acid (abbreviated as "HG" in Table 9) in the supernatant was determined by HPLC in the same manner as in Example 1. The results are shown in Table 9.

TABLE 9

| | | Yield (mM) | | | |
|---|---|---|---|---|---|
| | | | | HG | |
| | | KHG | | Threo- | Erythro- |
| Strain | Heat treatment | L-form | D-form | form | form |
| Bacillus sp. OC187 | not done | 7.7 | 28.8 | 2.8 | 11.4 |
| | done | 0.0 | 27.6 | 0.0 | 10.0 |

EXAMPLE 15

In the same manner as in Example 11, cells of Bacillus sp. S16 (FERM BP-4647) were put into 10 test tubes each filled with 10 ml of GMSG medium, and the cultivation was carried out at 30° C. for 20 hours. The cells in these 10 test tubes were collected by centrifugation, and suspended in 10 ml of reaction mixture (a). The reaction was carried out at 30° C. for 5 hours. The reaction mixture was centrifuged to obtain a supernatant. The supernatant was analyzed by HPLC using a SUMICHIRAL OA-5000 column (manufactured by Sumitomo Chemical Co., Ltd.). As a result, it was found that 40.6 mM of D-4-hydroxy-2-ketoglutaric acid was formed in the supernatant. L-4-hydroxy-2-ketoglutaric acid was not detected. 2.5 ml of the supernatant was put into each of 4 thick sterilized test tubes. Further, 0.5 ml of MSC medium having the composition mentioned below, 0.5 ml of a 50% glucose solution and 1 ml of a 10% ammonium chloride solution were sterilized and added to each of the test tubes. Still further, 0.5 ml of a culture of Arthrobacter protophormiae ATCC 19271 which was cultured overnight at 30° C. in a test tube filled with 3 ml of L medium was put into one of the test tubes, 0.5 ml of a culture of Pseudomonas chlororaphis ATCC 9446 which was cultivated in the same manner as mentioned above was put into one of the test tubes, 0.5 ml of a culture of *Serratia marcesens* ATCC 13880 which was cultivated in the same manner as mentioned above was put into one of the test tubes, and 0.5 ml of a culture of *Corynebacterium glutamicum* ATCC 13032 which was cultivated in the same manner as mentioned above was put into one of the test tubes, respectively. These were cultivated at 30° C. for 48 hours. After the completion of the culturing, the cells were removed by centrifugation, and the amount of γ-hydroxy-L-glutamic acid in the supernatant was determined by HPLC in the same manner as in Example 1. The results are shown in Table 10.

Composition of MSG medium (amounts per liter):

| | |
|---|---|
| $KH_2PO_4$ | 20 g |
| $(NH_4)_2SO_4$ | 20 g |
| $FeSO_4.7H_2O$ | 50 mg |
| $MnSO_4.7H_2O$ | 20 mg |
| $MgSO_4.7H_2O$ | 5 g |
| $CaCl_2$ | 100 mg |
| Yeast extract | 10 g |
| Peptone | 10 g |
| pH | 7.0 |

TABLE 10

| | Yield of γ-hydoxy-L-glutamic acid (mM) | |
|---|---|---|
| Strains | Threo-form | Erythro-form |
| *Arthrobacter protophomiae* ATCC 19271 | 0.0 | 6.0 |
| *Pseudomonas chlororaphis* ATCC 9446 | 0.0 | 15.8 |
| *Serratia marcesens* ATCC 13880 | 0.0 | 7.8 |
| *Corynebacterium glutamicum* ATCC 13032 | 0.0 | 5.8 |

EXAMPLE 16

*Bacillus* sp. S16 (FERM BP-4647) was inoculated in 9 ml of L medium, and cultivated at 30° C. for 16 hours with shaking. The whole amount of the culture was inoculated in 300 ml of GMSG medium, and cultivated in a 2-liter conical flask at 30° C. for 20 hours with shaking. From the obtained culture, the cells were collected by centrifugation, and suspended in 60 ml of reaction mixture (a). The reaction was carried out in a 300-milliliter beaker with stirring. After 6 hours from the starting point of the reaction, 3 ml of a 2M sodium pyruvate solution and 3 ml of a 2M sodium glyoxylate solution were added thereto. After 24 hours from the starting point of the reaction, the cells were removed from the reaction mixture by centrifugation to obtain the supernatant of the first reaction mixture.

Meanwhile, E. coli HKK27/pHK10 was cultivated in L medium containing 10 mg/liter of tetracycline overnight at 37° C. The whole amount of the culture was added to a 2-liter conical flask filled with 750 ml of M9 medium supplemented with 0.4% glucose, 0.05% of succinic acid, 0.2% ammonium sulfate, 100 mg/liter L-tryptophan, 0.1% yeast extract, 0.1% peptone and 10 mg/liter tetracycline. The mixture was cultivated at 37° C. for 8 hours. From the obtained culture, the supernatant was removed by centrifugation, and the cells were suspended in sterilized water such that the concentration of the wet cells reached 100 g/liter.

Eight milliliter of the obtained E. coli HKK27/pHK10 suspension, 4.8 ml of a 50% glucose solution, 4 ml of a 20% ammonium sulfate solution, 8 ml of M9C solution and 5.2 ml of sterilized water were added to 50 ml of the above-obtained first reaction mixture. The second reaction was carried out with stirring the mixture in a 300-ml beaker. During the second reaction, the pH was maintained at 7 with 7% aqueous ammonia. After 12 hours from the starting point of the reaction, the cells were removed by centrifugation, and the amount of γ-hydroxy-L-glutamic acid in the supernatant was determined by HPLC using an ODS column (manufactured by Merck). As a result, 8.6 g/liter of erythro-γ-hydroxy-L-glutamic acid was detected.

EXAMPLE 17

The supernatant (75 ml) in the second reaction mixture obtained in Example 14 was passed through a column of a strongly acidic cation exchange resin [DoweX 50×8 (Na-type), manufactured by Dow Chemical Company]. Erythro-γ-hydroxy-L-glutamic acid was eluted with ammonia, concentrated, and crystallized to obtain 0.5 g of erythro-γ-hydroxy-L-glutamic acid crystals.

EFFECTS OF THE INVENTION

The present invention provides an optically active γ-hydroxy-L-glutamic acid advantageously on an industrial scale, the optically active γ-hydroxy-L-glutamic acid being known to have activity of inhibiting glutamine synthetase activity or incorporation of glutamic acid by presynaptic vesicle and being useful as a reagent for investigation of the above-mentioned enzyme or organ and as a medicament based on this activity.

What is claimed is:

1. A process for producing an optical active γ-hydroxy-L-glutamic acid, which comprises:

(a) adding an amino group donor, pyruvic acid and glyoxylic acid to an aqueous medium containing a biocatalyst (hereinafter referred to as "biocatalyst I") to form an optically active γ-hydroxy-L-glutamic acid in the aqueous medium, and (b) recovering said optically active γ-hydroxy-L-glutamic acid therefrom;

wherein said biocatalyst I has an activity of forming an optically active γ-hydroxy-L-glutamic acid from pyruvic acid and glyoxylic acid in the presence of an amino group donor and is derived from a microorganism belonging to the genus *Pseudomonas, Paracoccus, Providencia, Rhizobium, Morganella, Enterobacter, Arthrobacter, Caulobacter, Microbacterium, Curtobacterium, Brevibacterium, Corynebacterium, Clavibacter* or *Bacillus*.

2. A process for producing an optically active γ-hydroxy-L-glutamic acid, which comprises:

(a) adding an amino acid donor and an optically active 4-hydroxy-2-ketoglutaric acid to an aqueous medium containing a biocatalyst (hereinafter referred to as "biocatalyst II") to form an optically active γ-hydroxy-L-glutamic acid in the aqueous medium, and (b) recovering said optically active γ-hydroxy-L-glutamic acid therefrom;

wherein said biocatalyst II has an activity of forming an optically active γ-hydroxy-L-glutamic acid from optically active 4-hydroxy-2-ketoglutaric acid in the presence of an amino group donor and is derived from a microorganism belonging to the genus *Escherichia, Serratia, Pseudomonas, Arthrobacter* or *Corynebacterium*.

3. The process of claim 1 or 2 wherein the optically active γ-hydroxy-L-glutamic acid is threo-γ-hydroxy-L-glutamic acid [(2S,4S)-4-hydroxyglutamic acid] or erythro-γ-hydroxy-L-glutamic acid [(2S,4R)-4-hydroxyglutamic acid].

4. The process of claim 1 wherein pyruvic acid is formed from a compound capable of being converted into pyruvic acid by biocatalyst I.

5. The process of claim 4 wherein the compound capable of being converted into pyruvic acid by biocatalyst I is glucose, fructose, maltose, glycerol, lactic acid or ammonium lactate.

6. The process of claim 1, wherein biocatalyst I is a culture, cells or processed cells of a microorganism.

7. The process of claim 6 wherein the optically active γ-hydroxy-L-glutamic acid is threo-γ-hydroxy-L-glutamic acid, and the microorganism is a microorganism belonging to the genus *Pseudomonas, Paracoccus, Providencia, Rhizobium, Microbacterium, Enterobacter, Arthrobacter, Caulobacter, Microbacterium, Curtobacterium, Brevibacterium, Corynebacterium* or *Clavibacter.*

8. The process of claim 6 wherein the optically active γ-hydroxy-L-glutamic acid is erythro-γ-hydroxy-L-glutamic acid, and the microorganism is a microorganism belonging to the genus *Bacillus.*

9. The process of claim 2 wherein the optically active 4-hydroxy-2-ketoglutaric acid is L-4-hydroxy-2-ketoglutaric acid [(S)-4-hydroxy-2-ketoglutaric acid] or D-4-hydroxy-2-ketoglutaric acid [(R)-4-hydroxy-2-ketoglutaric acid].

10. The process of claim 2 wherein biocatalyst II is a culture, cells or processed cells of a microorganism.

11. The process of claim 10 wherein the microorganism is a strain in which at least one of α-ketoglutaric acid dehydrogenase (α-ketoglutarate dehydrogenase) activity and optically active 4-hydroxy-2-ketoglutaric acid degrading activity is decreased or deleted.

12. The process of claim 7, 8 or 11 wherein the microorganism is a strain having increased glutamic acid dehydrogenase activity.

13. The process of claim 2, 9, 10, 11 wherein the optically active 4-hydroxy-2-ketoglutaric acid is formed by adding pyruvic acid and glyoxylic acid to an aqueous medium containing a biocatalyst (hereinafter referred to as "biocatalyst III"), wherein said biocatalyst III has an activity of forming an optically active 4-hydroxy-2-ketoglutaric acid from pyruvic acid and glyoxylic acid and is derived from a microorganism belonging to the genus *Cellvibrio, Bacillus, Pseudomonas, Paracoccus, Providencia, Rhizobium* or *Morganella.*

14. The process of claim 13 wherein biocatalyst III is a culture, cells or processed cells of a microorganism.

15. The process of claim 14 wherein the microorganism is a microorganism belonging to the genus *Cellvibrio* or *Bacillus* and having activity of forming D-4-hydroxy-2-ketoglutaric acid from pyruvic acid and glyoxylic acid.

16. The process of claim 14 wherein the microorganism is a microorganism belonging to the genus *Pseudomonas, Paracoccus, Providencia, Rhizobium,* or *Morganella* and having activity of forming L-4-hydroxy-2-ketoglutaric acid from pyruvic acid and glyoxylic acid.

* * * * *